US010357320B2

(12) United States Patent
Beira

(10) Patent No.: US 10,357,320 B2
(45) Date of Patent: Jul. 23, 2019

(54) SURGICAL SYSTEM FOR MICROSURGICAL TECHNIQUES

(71) Applicants: DistalMotion SA, Lausanne (CH); Ricardo Daniel Rita Beira, Lausanne (CH)

(72) Inventor: Ricardo Daniel Rita Beira, Lausanne (CH)

(73) Assignee: DistalMotion SA, Epalinges (CH)

( * ) Notice: Subject to any disclaimer, the term of this patent is extended or adjusted under 35 U.S.C. 154(b) by 131 days.

(21) Appl. No.: 15/506,659

(22) PCT Filed: Aug. 27, 2015

(86) PCT No.: PCT/IB2015/002095
§ 371 (c)(1),
(2) Date: Feb. 24, 2017

(87) PCT Pub. No.: WO2016/030767
PCT Pub. Date: Mar. 3, 2016

(65) Prior Publication Data
US 2017/0245954 A1 Aug. 31, 2017

Related U.S. Application Data

(60) Provisional application No. 62/042,789, filed on Aug. 27, 2014.

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/70* (2016.02); *A61B 34/77* (2016.02); *A61B 90/20* (2016.02); *A61B 2090/3616* (2016.02)

(58) Field of Classification Search
CPC ......... A61B 34/37; A61B 34/70; A61B 34/77; A61B 90/20; A61B 2090/3616
(Continued)

(56) References Cited

U.S. PATENT DOCUMENTS 2,764,301 A 9/1956 Goertz et al.
2,771,199 A 11/1956 Jelatis
(Continued)

FOREIGN PATENT DOCUMENTS

CN 101584594 A 11/2009
CN 101637402 A 2/2010
(Continued)

OTHER PUBLICATIONS

Abbott, et al., "Design of an Endoluminal Notes Robotic System," IEEE/RSJ International Conference on Intelligent Robots and Systems, San Diego, CA, pp. 410-416 (2007).
(Continued)

*Primary Examiner* — Jaime Figueroa
(74) *Attorney, Agent, or Firm* — Foley & Lardner LLP; Christopher C. Bolten; Nicola A. Pisano

(57) ABSTRACT

This system is composed by mechanical telemanipulators, with master-slave configurations, working together with suitable solutions for image acquisition and display, which are able to transmit, with optional magnification, images from the surgical area to the surgeon. Therefore, the surgeon's capacities and comfort are increased by enhancing the surgeon's motor and visual skills as well as the ergonomics while doing different surgical tasks through access incisions on the patient body. Aside from offering improved performance during procedures involving microsurgical techniques, this system also brings safety, intuitiveness, and cost-effectiveness advantages over current alternatives. Due to the compatibility with current visualization systems for microsurgery, together with the light weight and the compact configuration of the mechanical telemanipulator, this surgical system can be very easily brought to and removed from the surgical area, which enables its intermittent use on several surgical procedures requiring microsurgical tech-
(Continued)

niques. Therefore, it does not require drastic changes in the workflow and setup of current operating rooms and can be more easily adopted by several surgical teams.

16 Claims, 13 Drawing Sheets

(51) Int. Cl.
    *A61B 90/20* (2016.01)
    *A61B 90/00* (2016.01)

(58) Field of Classification Search
    USPC .......................................................... 700/245
    See application file for complete search history.

(56) References Cited

U.S. PATENT DOCUMENTS

| | | | |
|---|---|---|---|
| 2,774,488 A | 12/1956 | Goertz | |
| 2,846,084 A | 8/1958 | Goertz et al. | |
| 3,065,863 A | 11/1962 | Saunders, Jr. | |
| 3,095,096 A | 6/1963 | Chesley | |
| 3,212,651 A | 10/1965 | Specht et al. | |
| 3,261,480 A | 7/1966 | Haaker et al. | |
| 3,297,172 A | 1/1967 | Haaker et al. | |
| 3,391,801 A | 7/1968 | Haaker | |
| 3,425,569 A | 2/1969 | Haaker et al. | |
| 4,221,516 A | 9/1980 | Haaker et al. | |
| 4,756,655 A | 7/1988 | Jameson | |
| 5,147,357 A | 9/1992 | Rose et al. | |
| 5,176,352 A | 1/1993 | Braun | |
| 5,207,114 A | 5/1993 | Salisbury et al. | |
| 5,209,747 A | 5/1993 | Knoepfler | |
| 5,304,203 A | 4/1994 | El-Mallawany et al. | |
| 5,308,358 A | 5/1994 | Bond et al. | |
| 5,330,502 A | 7/1994 | Hassler et al. | |
| 5,368,606 A | 11/1994 | Marlow et al. | |
| 5,383,888 A | 1/1995 | Zvenyatsky et al. | |
| 5,484,435 A | 1/1996 | Fleenor et al. | |
| 5,599,151 A | 2/1997 | Daum et al. | |
| 5,603,723 A | 2/1997 | Aranyi et al. | |
| 5,631,973 A | 5/1997 | Green | |
| 5,649,956 A | 7/1997 | Jensen et al. | |
| 5,710,870 A | 1/1998 | Ohm et al. | |
| 5,716,352 A | 2/1998 | Viola et al. | |
| 5,735,874 A | 4/1998 | Measamer et al. | |
| 5,784,542 A | 7/1998 | Ohm et al. | |
| 5,797,900 A | 8/1998 | Madhani et al. | |
| 5,810,716 A | 9/1998 | Mukherjee et al. | |
| 5,810,805 A | 9/1998 | Sutcu et al. | |
| 5,828,813 A | 10/1998 | Ohm | |
| 5,908,436 A | 6/1999 | Cuschieri et al. | |
| 5,951,587 A | 9/1999 | Qureshi et al. | |
| 6,026,701 A | 2/2000 | Reboulet | |
| 6,197,017 B1 | 3/2001 | Brock et al. | |
| 6,206,903 B1 | 3/2001 | Ramans | |
| 6,233,504 B1 | 5/2001 | Das et al. | |
| 6,281,651 B1 | 8/2001 | Haanpaa et al. | |
| 6,358,249 B1 | 3/2002 | Chen et al. | |
| 6,361,534 B1 | 3/2002 | Chen et al. | |
| 6,364,879 B1 | 4/2002 | Chen et al. | |
| 6,371,952 B1 | 4/2002 | Madhani et al. | |
| 6,394,998 B1 | 5/2002 | Wallace et al. | |
| 6,435,794 B1 | 8/2002 | Springer | |
| 6,436,107 B1 * | 8/2002 | Wang .................. | A61B 1/00149 318/568.11 |
| 6,554,844 B2 | 4/2003 | Lee et al. | |
| 6,786,896 B1 | 9/2004 | Madhani et al. | |
| 6,788,999 B2 | 9/2004 | Green | |
| 6,850,817 B1 | 2/2005 | Green | |
| 6,852,107 B2 | 2/2005 | Wang et al. | |
| 6,902,560 B1 | 6/2005 | Morley et al. | |
| 6,951,535 B2 | 10/2005 | Ghodoussi et al. | |
| 6,991,627 B2 | 1/2006 | Madhani et al. | |
| 6,994,708 B2 | 2/2006 | Manzo | |
| 7,090,637 B2 | 8/2006 | Danitz et al. | |
| 7,101,363 B2 | 9/2006 | Nishizawa et al. | |
| 7,204,836 B2 | 4/2007 | Wagner et al. | |
| 7,232,440 B2 | 6/2007 | Dumbauld et al. | |
| 7,306,597 B2 | 12/2007 | Manzo | |
| 7,316,681 B2 | 1/2008 | Madhani et al. | |
| 7,338,513 B2 | 3/2008 | Lee et al. | |
| 7,364,582 B2 | 4/2008 | Lee | |
| 7,398,707 B2 | 7/2008 | Morley et al. | |
| 7,481,824 B2 | 1/2009 | Boudreaux et al. | |
| 7,594,912 B2 | 9/2009 | Cooper et al. | |
| 7,608,039 B1 | 10/2009 | Todd | |
| 7,615,002 B2 | 11/2009 | Rothweiler et al. | |
| 7,615,067 B2 | 11/2009 | Lee et al. | |
| 7,674,255 B2 | 3/2010 | Braun | |
| 7,699,855 B2 | 4/2010 | Anderson et al. | |
| 7,819,894 B2 | 10/2010 | Mitsuishi et al. | |
| 7,824,401 B2 | 11/2010 | Manzo et al. | |
| 7,828,798 B2 | 11/2010 | Buysse et al. | |
| 7,976,458 B2 | 7/2011 | Stefanchik et al. | |
| 8,048,084 B2 | 11/2011 | Schneid | |
| 8,105,320 B2 | 1/2012 | Manzo | |
| 8,114,017 B2 | 2/2012 | Bacher | |
| 8,137,263 B2 | 3/2012 | Marescaux et al. | |
| 8,224,485 B2 | 7/2012 | Unsworth | |
| 8,287,469 B2 | 10/2012 | Stefanchik et al. | |
| 8,292,889 B2 | 10/2012 | Cunningham et al. | |
| 8,306,656 B1 | 11/2012 | Schaible et al. | |
| 8,308,738 B2 | 11/2012 | Nobis et al. | |
| 8,332,072 B1 | 12/2012 | Schaible et al. | |
| 8,336,751 B2 | 12/2012 | Scirica | |
| 8,347,754 B1 | 1/2013 | Veltri et al. | |
| 8,353,898 B2 | 1/2013 | Lutze et al. | |
| 8,357,161 B2 | 1/2013 | Mueller | |
| 8,382,742 B2 | 2/2013 | Hermann et al. | |
| 8,403,832 B2 | 3/2013 | Cunningham et al. | |
| 8,418,904 B2 | 4/2013 | Wenchell et al. | |
| 8,496,152 B2 | 7/2013 | Viola | |
| 8,523,900 B2 | 9/2013 | Jinno et al. | |
| 8,540,748 B2 | 9/2013 | Murphy et al. | |
| 8,562,592 B2 | 10/2013 | Conlon et al. | |
| 8,568,444 B2 | 10/2013 | Cunningham | |
| 8,579,176 B2 | 11/2013 | Smith et al. | |
| 8,591,397 B2 | 11/2013 | Berkelman et al. | |
| 8,603,077 B2 | 12/2013 | Cooper et al. | |
| 8,617,203 B2 | 12/2013 | Stefanchik et al. | |
| 8,663,270 B2 | 3/2014 | Donnigan et al. | |
| 8,668,689 B2 | 3/2014 | Dumbauld et al. | |
| 8,668,702 B2 | 3/2014 | Awtar et al. | |
| 8,696,666 B2 | 4/2014 | Sanai et al. | |
| 8,709,000 B2 | 4/2014 | Madhani et al. | |
| 8,768,509 B2 | 7/2014 | Unsworth | |
| 8,792,688 B2 | 7/2014 | Unsworth | |
| 8,801,752 B2 | 8/2014 | Fortier et al. | |
| 8,818,560 B2 | 8/2014 | Kishi | |
| 8,821,480 B2 | 9/2014 | Burbank | |
| 8,828,046 B2 | 9/2014 | Stefanchik et al. | |
| 8,845,517 B2 | 9/2014 | Russo | |
| 8,845,622 B2 | 9/2014 | Paik et al. | |
| 8,870,867 B2 | 10/2014 | Walberg et al. | |
| 8,887,979 B2 | 11/2014 | Mastri et al. | |
| 8,894,674 B2 | 11/2014 | Balanev et al. | |
| 8,930,027 B2 | 1/2015 | Schaible et al. | |
| 8,945,098 B2 | 2/2015 | Seibold et al. | |
| 8,961,499 B2 | 2/2015 | Paik et al. | |
| 8,961,514 B2 | 2/2015 | Garrison | |
| 8,968,187 B2 | 3/2015 | Kleyman et al. | |
| 8,989,844 B2 | 3/2015 | Cinquin et al. | |
| 8,992,564 B2 | 3/2015 | Jaspers | |
| 9,023,015 B2 | 5/2015 | Penna | |
| 9,033,998 B1 | 5/2015 | Schaible et al. | |
| 9,044,238 B2 | 6/2015 | Orszulak | |
| 9,084,606 B2 | 7/2015 | Greep | |
| 9,113,861 B2 | 8/2015 | Martin et al. | |
| 9,149,339 B2 | 10/2015 | Unsworth | |
| 9,307,894 B2 | 4/2016 | Von Grunberg et al. | |
| 9,474,580 B2 * | 10/2016 | Hannaford ............ | A61B 90/60 |
| 9,480,531 B2 | 11/2016 | Von Grunberg | |
| 9,492,240 B2 * | 11/2016 | Itkowitz ................ | A61B 34/37 |

(56) References Cited

U.S. PATENT DOCUMENTS

| | | | |
|---|---|---|---|
| 9,696,700 B2* | 7/2017 | Beira | A61B 17/00234 |
| 10,092,359 B2 | 10/2018 | Coe et al. | |
| 2002/0040217 A1 | 4/2002 | Jinno | |
| 2002/0049367 A1 | 4/2002 | Irion et al. | |
| 2002/0072736 A1 | 6/2002 | Tierney et al. | |
| 2003/0155747 A1 | 8/2003 | Bridges | |
| 2003/0208186 A1 | 11/2003 | Moreyra | |
| 2004/0049205 A1 | 3/2004 | Lee et al. | |
| 2004/0116906 A1* | 6/2004 | Lipow | A61B 34/70 606/1 |
| 2004/0236316 A1 | 11/2004 | Danitz et al. | |
| 2004/0253079 A1 | 12/2004 | Sanchez | |
| 2005/0096502 A1 | 5/2005 | Khalili | |
| 2005/0204851 A1 | 9/2005 | Morley et al. | |
| 2005/0240078 A1 | 10/2005 | Kwon et al. | |
| 2006/0043698 A1 | 3/2006 | Bridges | |
| 2006/0178559 A1* | 8/2006 | Kumar | A61B 34/37 600/109 |
| 2006/0183975 A1 | 8/2006 | Saadat et al. | |
| 2006/0219065 A1 | 10/2006 | Jinno et al. | |
| 2006/0235436 A1 | 10/2006 | Anderson et al. | |
| 2006/0253109 A1 | 11/2006 | Chu | |
| 2007/0088340 A1 | 4/2007 | Brock et al. | |
| 2007/0137371 A1* | 6/2007 | Devengenzo | B25J 15/04 74/490.01 |
| 2007/0156123 A1 | 7/2007 | Moll et al. | |
| 2007/0208375 A1 | 9/2007 | Nishizawa et al. | |
| 2007/0299387 A1 | 12/2007 | Williams et al. | |
| 2008/0039255 A1 | 2/2008 | Jinno et al. | |
| 2008/0046122 A1 | 2/2008 | Manzo et al. | |
| 2008/0058776 A1 | 3/2008 | Jo et al. | |
| 2008/0071208 A1 | 3/2008 | Voegele et al. | |
| 2008/0103492 A1 | 5/2008 | Morley et al. | |
| 2008/0177285 A1 | 7/2008 | Brock et al. | |
| 2008/0243106 A1 | 10/2008 | Coe et al. | |
| 2008/0314181 A1 | 12/2008 | Schena | |
| 2009/0036902 A1* | 2/2009 | DiMaio | A61B 34/10 606/130 |
| 2009/0198253 A1 | 8/2009 | Omori | |
| 2009/0216249 A1 | 8/2009 | Jinno et al. | |
| 2009/0247821 A1 | 10/2009 | Rogers | |
| 2009/0248039 A1 | 10/2009 | Cooper et al. | |
| 2009/0299141 A1 | 12/2009 | Downey et al. | |
| 2010/0004508 A1 | 1/2010 | Naito et al. | |
| 2010/0011900 A1* | 1/2010 | Burbank | A61B 34/71 74/490.06 |
| 2010/0023025 A1 | 1/2010 | Zeiner et al. | |
| 2010/0094130 A1* | 4/2010 | Ninomiya | A61B 8/00 600/437 |
| 2010/0121347 A1 | 5/2010 | Jaspers | |
| 2010/0160929 A1 | 6/2010 | Rogers et al. | |
| 2010/0160940 A1 | 6/2010 | Lutze et al. | |
| 2010/0170519 A1 | 7/2010 | Romo et al. | |
| 2010/0225209 A1* | 9/2010 | Goldberg | A61B 34/30 312/209 |
| 2010/0305595 A1 | 12/2010 | Hermann | |
| 2010/0318099 A1 | 12/2010 | Itkowitz et al. | |
| 2010/0318101 A1 | 12/2010 | Choi | |
| 2010/0331859 A1* | 12/2010 | Omori | A61B 17/4241 606/130 |
| 2011/0087236 A1 | 4/2011 | Stokes et al. | |
| 2011/0087238 A1* | 4/2011 | Wang | A61B 17/11 606/130 |
| 2011/0213346 A1 | 9/2011 | Morley et al. | |
| 2011/0230867 A1 | 9/2011 | Hirschfeld et al. | |
| 2011/0275901 A1 | 11/2011 | Shelton, IV | |
| 2011/0276084 A1 | 11/2011 | Shelton, IV | |
| 2011/0290854 A1 | 12/2011 | Timm et al. | |
| 2011/0301419 A1 | 12/2011 | Craft et al. | |
| 2012/0027762 A1 | 2/2012 | Schofield | |
| 2012/0031114 A1 | 2/2012 | Mueller et al. | |
| 2012/0049623 A1 | 3/2012 | Nakayama | |
| 2012/0095298 A1 | 4/2012 | Stefanchik et al. | |
| 2012/0116163 A1 | 5/2012 | Lutze et al. | |
| 2012/0132018 A1 | 5/2012 | Tang et al. | |
| 2012/0143173 A1 | 6/2012 | Steege et al. | |
| 2012/0158014 A1 | 6/2012 | Stefanchik et al. | |
| 2012/0209292 A1 | 8/2012 | Devengenzo et al. | |
| 2012/0253326 A1 | 10/2012 | Kleyman | |
| 2012/0277762 A1 | 11/2012 | Lathrop et al. | |
| 2012/0283745 A1* | 11/2012 | Goldberg | A61B 34/30 606/130 |
| 2012/0289973 A1 | 11/2012 | Prisco et al. | |
| 2012/0289974 A1 | 11/2012 | Rogers et al. | |
| 2012/0296341 A1 | 11/2012 | Seibold et al. | |
| 2013/0123805 A1 | 5/2013 | Park et al. | |
| 2013/0144274 A1 | 6/2013 | Stefanchik et al. | |
| 2013/0172713 A1 | 7/2013 | Kirschenman | |
| 2013/0245643 A1 | 9/2013 | Woodard et al. | |
| 2013/0245647 A1 | 9/2013 | Martin et al. | |
| 2013/0282027 A1 | 10/2013 | Woodard et al. | |
| 2013/0303408 A1 | 11/2013 | Indermuhle | |
| 2013/0304083 A1 | 11/2013 | Kaercher et al. | |
| 2013/0304084 A1 | 11/2013 | Beira et al. | |
| 2014/0005681 A1 | 1/2014 | Gee et al. | |
| 2014/0018447 A1 | 1/2014 | McGovern et al. | |
| 2014/0018780 A1 | 1/2014 | Hirscheld | |
| 2014/0076088 A1 | 3/2014 | Berkelman et al. | |
| 2014/0114481 A1 | 4/2014 | Ogawa et al. | |
| 2014/0135794 A1* | 5/2014 | Cau | A61B 34/75 606/130 |
| 2014/0142595 A1 | 5/2014 | Awtar et al. | |
| 2014/0166023 A1 | 6/2014 | Kishi | |
| 2014/0180308 A1 | 6/2014 | Von Grunberg | |
| 2014/0188091 A1 | 7/2014 | Vidal et al. | |
| 2014/0188159 A1 | 7/2014 | Steege | |
| 2014/0195010 A1* | 7/2014 | Beira | A61B 17/00234 700/3 |
| 2014/0200561 A1 | 7/2014 | Ingmanson et al. | |
| 2014/0207150 A1 | 7/2014 | Rosa et al. | |
| 2014/0230595 A1 | 8/2014 | Butt et al. | |
| 2014/0249546 A1 | 9/2014 | Shvartsberg et al. | |
| 2014/0263541 A1 | 9/2014 | Leimbach et al. | |
| 2014/0263553 A1 | 9/2014 | Leimbach et al. | |
| 2014/0276950 A1 | 9/2014 | Smaby et al. | |
| 2014/0276951 A1 | 9/2014 | Hourtash et al. | |
| 2014/0276956 A1 | 9/2014 | Crainich et al. | |
| 2014/0350570 A1 | 11/2014 | Lee | |
| 2015/0057499 A1 | 2/2015 | Erden et al. | |
| 2015/0057702 A1 | 2/2015 | Edmondson et al. | |
| 2015/0060517 A1 | 3/2015 | Williams | |
| 2015/0066018 A1 | 3/2015 | Doll et al. | |
| 2015/0105821 A1 | 4/2015 | Ward et al. | |
| 2015/0113933 A1 | 4/2015 | Markt | |
| 2015/0142018 A1 | 5/2015 | Sniffin et al. | |
| 2015/0150575 A1 | 6/2015 | Hartoumbekis et al. | |
| 2015/0250547 A1 | 9/2015 | Fukushima et al. | |
| 2015/0265355 A1 | 9/2015 | Prestel et al. | |
| 2016/0022365 A1 | 1/2016 | Jensen et al. | |
| 2016/0051274 A1 | 2/2016 | Howell et al. | |
| 2016/0151115 A1 | 6/2016 | Karguth et al. | |
| 2016/0346053 A1 | 12/2016 | Beira | |
| 2016/0374766 A1 | 12/2016 | Schuh | |
| 2017/0245954 A1 | 8/2017 | Beira | |
| 2017/0273749 A1 | 9/2017 | Grover et al. | |
| 2017/0308667 A1 | 10/2017 | Beira et al. | |
| 2017/0360522 A1 | 12/2017 | Beira | |
| 2017/0367778 A1 | 12/2017 | Beira | |
| 2018/0000472 A1 | 1/2018 | Beira | |
| 2018/0000544 A1 | 1/2018 | Beira | |
| 2018/0000550 A1 | 1/2018 | Beira | |
| 2018/0055583 A1 | 3/2018 | Schuh et al. | |
| 2018/0125519 A1 | 5/2018 | Beira et al. | |
| 2018/0353252 A1 | 12/2018 | Chassot et al. | |

FOREIGN PATENT DOCUMENTS

| | | |
|---|---|---|
| CN | 101732093 A | 6/2010 |
| CN | 103717355 A | 4/2014 |
| DE | 43 03 311 A1 | 8/1994 |
| DE | 19652792 C2 | 5/1999 |
| DE | 10314827 B3 | 4/2004 |
| DE | 10314828 B3 | 7/2004 |

(56) References Cited

FOREIGN PATENT DOCUMENTS

| | | |
|---|---|---|
| DE | 10 2012 222 755 | 6/2014 |
| DE | 10 2014 205 036 A1 | 9/2015 |
| DE | 10 2014 205 159 A1 | 9/2015 |
| EP | 0 595 291 A1 | 5/1994 |
| EP | 0 621 009 A1 | 10/1994 |
| EP | 0 677 275 A2 | 10/1995 |
| EP | 0 776 739 A2 | 6/1997 |
| EP | 1 254 642 A1 | 11/2002 |
| EP | 1 279 371 B1 | 12/2004 |
| EP | 1 886 630 A2 | 2/2008 |
| EP | 1 889 579 A2 | 2/2008 |
| EP | 2 058 090 A2 | 5/2009 |
| EP | 1 977 677 B1 | 8/2009 |
| EP | 2 095 778 A1 | 9/2009 |
| EP | 1 889 583 B1 | 4/2011 |
| EP | 2 377 477 B1 | 5/2012 |
| EP | 2 473 119 A2 | 7/2012 |
| EP | 2 305 144 B1 | 10/2012 |
| EP | 2 044 893 B1 | 7/2013 |
| EP | 2 653 110 A1 | 10/2013 |
| EP | 2 679 192 A2 | 1/2014 |
| EP | 2 736 680 A2 | 6/2014 |
| EP | 2 777 561 A1 | 9/2014 |
| EP | 2 837 340 A1 | 2/2015 |
| EP | 2 837 354 A1 | 2/2015 |
| EP | 2 554 131 B1 | 8/2015 |
| EP | 2 979 657 A1 | 2/2016 |
| GB | 0 969 899 A | 9/1964 |
| JP | 2004-041580 A | 2/2004 |
| JP | 2007-290096 A | 11/2007 |
| JP | 2008-104620 A | 5/2008 |
| JP | 2009-018027 A | 1/2009 |
| KR | 20110032444 A | 3/2011 |
| KR | 20130031403 A | 3/2013 |
| WO | WO-82/00611 A1 | 3/1982 |
| WO | WO-97/43942 A1 | 11/1997 |
| WO | WO-98/25666 A1 | 6/1998 |
| WO | WO-03/067341 A2 | 8/2003 |
| WO | WO-03/086219 A2 | 10/2003 |
| WO | WO-2004/052171 A2 | 6/2004 |
| WO | WO-2005/009482 A2 | 2/2005 |
| WO | WO-2005/046500 A1 | 5/2005 |
| WO | WO-2006/086663 A2 | 4/2006 |
| WO | WO-2007/133065 A1 | 11/2007 |
| WO | WO-2008/130235 A2 | 10/2008 |
| WO | WO-2009/091497 A2 | 7/2009 |
| WO | WO-2009/095893 A2 | 8/2009 |
| WO | WO-2009/145572 A2 | 12/2009 |
| WO | WO-2009/157719 A2 | 12/2009 |
| WO | WO-2010/019001 A2 | 2/2010 |
| WO | WO-2010/030114 A2 | 3/2010 |
| WO | WO-2010/050771 A2 | 5/2010 |
| WO | WO-2010/083480 A2 | 7/2010 |
| WO | WO-2010/096580 A1 | 8/2010 |
| WO | WO-2010/130817 A1 | 11/2010 |
| WO | WO-2011/027183 A1 | 3/2011 |
| WO | WO-2011/123669 A1 | 10/2011 |
| WO | WO-2012/020386 A1 | 2/2012 |
| WO | WO-2012/049623 A1 | 4/2012 |
| WO | WO-2013/007784 A1 | 1/2013 |
| WO | WO-2013/014621 A1 | 1/2013 |
| WO | WO-2013/014621 A2 | 1/2013 |
| WO | WO-2014/012780 A1 | 1/2014 |
| WO | WO-2014/018447 A1 | 1/2014 |
| WO | WO-2014/067804 A1 | 5/2014 |
| WO | WO-2014/094716 A1 | 6/2014 |
| WO | WO-2014/094717 | 6/2014 |
| WO | WO-2014/094718 | 6/2014 |
| WO | WO-2014/094719 | 6/2014 |
| WO | WO-2014/145148 A2 | 9/2014 |
| WO | WO-2014/156221 A1 | 10/2014 |
| WO | WO-2014/201010 A1 | 12/2014 |
| WO | WO-2014/201538 A1 | 12/2014 |
| WO | WO-2015/081946 A1 | 6/2015 |
| WO | WO-2015/081947 A1 | 6/2015 |
| WO | WO-2015/088647 A1 | 6/2015 |
| WO | WO-2015/088655 A1 | 6/2015 |
| WO | WO-2015/111475 A1 | 7/2015 |
| WO | WO-2015/113933 A1 | 8/2015 |
| WO | WO-2015/129383 A1 | 8/2015 |
| WO | WO-2015/139674 A1 | 9/2015 |
| WO | WO-2015/175200 A1 | 11/2015 |
| WO | WO-2016/030767 A9 | 3/2016 |
| WO | WO-2016/083189 A1 | 6/2016 |
| WO | WO-2016/097861 A1 | 6/2016 |
| WO | WO-2016/097864 A2 | 6/2016 |
| WO | WO-2016/097868 A1 | 6/2016 |
| WO | WO-2016/097871 A1 | 6/2016 |
| WO | WO-2016/097873 A2 | 6/2016 |
| WO | WO-2016/162751 A1 | 10/2016 |
| WO | WO-2016/162752 A1 | 10/2016 |
| WO | WO-2016/183054 A1 | 11/2016 |
| WO | WO-01/6189284 A1 | 12/2016 |
| WO | WO-2016/189284 A1 | 12/2016 |
| WO | WO-2017/015599 A1 | 1/2017 |
| WO | WO-2017/064301 A1 | 4/2017 |
| WO | WO-2017/064303 A1 | 4/2017 |
| WO | WO-2017/064305 A1 | 4/2017 |
| WO | WO-2017/064306 A1 | 4/2017 |

OTHER PUBLICATIONS

Aesculap Surgical Technologies, Aesculap® Caiman®, Advanced Bipolar Seal and Cut Technology Brochure, 6 pages (retrieved Aug. 31, 2015).

Arata, et al., "Development of a dexterous minimally-invasive surgical system with augmented force feedback capability," IEEE/RSJ International Conference on Intelligent Robots and Systems, pp. 3207-3212 (2005).

Çavuşoğlu, et al., "Laparoscopic Telesurgical Workstation," IEEE Transactions on Robotics and Automation,(15)4:728-739 (1999).

Dachs, et al., "Novel Surgical Robot Design: Minimizing the Operating Envelope Within the Sterile Field," 28th International Conference, IEEE Engineering in Medicine Biology Society, New York, pp. 1505-1508 (2006).

Dario, et al., "Novel Mechatronic Tool for Computer-Assisted Arthroscopy," IEEE Transactions on Information Technology in Biomedicine, 4(1):15-29 (Mar. 2000).

Focacci, et al., "Lightweight Hand-held Robot for Laparoscopic Surgery," IEEE International Conference on Robotics & Automation, Rome, Italy, pp. 599-604 (2007).

Guthart, et al., "The Intuitive™ Telesurgery System: Overview and Application," IEEE International Conference on Robotics & Automation, San Francisco, CA, pp. 618-621 (2000).

Ikuta, et al., "Development of Remote Microsurgery Robot and New Surgical Procedure for Deep and Narrow Space," IEEE International Conference on Robotics & Automation, Taipei, Taiwan, pp. 1103-1108 (2003).

Ikuta, et al., "Hyper Redundant Miniature Manipulator 'Hyper Finger' for Remote Minimally Invasive Surgery in Deep Area," IEEE International Conference on Robotics & Automation, Taipei, Taiwan, pp. 1098-1102 (2003).

International Search Report & Written Opinion dated Feb. 2, 2017 in Int'l PCT Patent Appl. Serial No. PCT/IB2016/001286.

International Search Report & Written Opinion dated Jan. 18, 2013 in Int'l PCT Patent Appl Serial No. PCT/IB2012/053786.

International Search Report dated Jan. 18, 2013 in Int'l PCT Patent Appl Serial No. PCT/IB2012/053786.

International Search Report dated Mar. 23, 2012 in Int'l PCT Patent Appl Serial No. PCT/IB2011/054476.

Ishii, et al., "Development of a New Bending Mechanism and Its Application to Robotic Forceps Manipulator," IEEE International Conference on Robotics & Automation, Rome, Italy, pp. 238-243 (2007).

International Search Report & Written Opinion dated May 23, 2016 in Int'l PCT Patent Appl Serial No. PCT/IB2015/002524.

International Search Report & Written Opinion dated Mar. 30, 2015 in Int'l PCT Patent Appl Serial No. PCT/EP2015/051473.

(56) References Cited

OTHER PUBLICATIONS

International Search Report & Written Opinion dated Apr. 26, 2016 in Int'l PCT Patent Appl Serial No. PCT/IB2015/002512.
International Search Report & Written Opinion dated May 24, 2016 in Int'l PCT Patent Appl Serial No. PCT/IB2015/002487.
International Search Report & Written Opinion dated Jun. 10, 2016 in Int'l PCT Patent Appl Serial No. PCT/IB2015/002533.
International Search Report & Written Opinion dated Jun. 13, 2016 in Int'l PCT Patent Appl Serial No. PCT/IB2015/002493.
International Search Report & Written Opinion dated Aug. 25, 2016 in Int'l PCT Patent Appl Serial No. PCT/IB2016/000542.
International Search Report & Written Opinion dated Sep. 2, 2016 in Int'l PCT Patent Appl Serial No. PCT/IB2016/000543.
Kobayashi, et al., "Small Occupancy Robotic Mechanisms for Endoscopic Surgery," International Conference on Medical Image Computing and Computer assisted Interventions, pp. 75-82 (2002).
Mayer, et al., "The Endo[PA]R System for Minimally Invasive Robotic Surgery," IEEE/RSJ International Conference on Intelligent Robots and Systems, Sendai, Japan, pp. 3637-3642 (2004).
Mitsuishi, et al., "Development of a Remote Minimally Invasive Surgical System with Operational Environment Transmission Capability," IEEE International Conference on Robotics & Automation, Taipei, Taiwan, pp. 2663-2670 (2003).
Nakamura, et al., "Multi-DOF Forceps Manipulator System for Laparoscopic Surgery-Mechanism miniaturized & Evaluation of New Interface," 4th International Conference on Medical Image Computing and Computer assisted Interventions (MICCAI2001), pp. 606-613 (2001).
Peirs, et al., "Design of an advanced tool guiding system for robotic surgery," IEEE International Conference on Robotics & Automation, Taipei, Taiwan, pp. 2651-2656 (2003).
Sallé, et al., "Optimal Design of High Dexterity Modular MIS Instrument for Coronary Artery Bypass Grafting," IEEE International Conference on Robotics & Automation, New Orleans, LA, pp. 1276-1281 (2004).
Seibold, et al., "Prototype of Instrument for Minimally Invasive Surgery with 6-Axis Force Sensing Capability," IEEE International Conference on Robotics & Automation, Barcelona, Spain, pp. 496-501 (2005).
Simaan et al., "Dexterous System for Laryngeal Surgery: Multi-Backbone Bending Snake-like Slaves for Teleoperated Dexterous Surgical Tool Manipulation," IEEE International Conference on Robotics & Automation, New Orleans, LA, pp. 351-357 (2004).
Stryker®, Endoscopy, Take a Look Around, Ideal Eyes™ FFD122 HD, Articulating Laparoscope Brochure, 2 pages (2009).
Swiss Search Report dated Jun. 4, 2012 in Swiss Patent Application No. CH 00702/12.
Tavakoli, et al., "Force Reflective Master-Slave System for Minimally Invasive Surgery," IEEE/RSJ International Conference on Intelligent Robots and Systems, Las Vegas, NV, pp. 3077-3082 (2003).
Taylor, et al., "Steady-Hand Robotic System for Microsurgical Augmentation," The International Journal of Robotics Research, 18(12):1201-1210 (1999).
www.cttc.co/technologies/maestro-non-robotic-dexterous-laproscopic-instrument-writs-providing-seven-degrees, "Maestro: Non-Robotic Dexterous Laproscopic Instrument With a Wrist Providing Seven Degrees of Freedom", accessed Nov. 12, 2015, 4 pages.
Yamashita, et al., "Development of Endoscopic Forceps Manipulator Using Multi-Slider Linkage Mechanisms," The 1st Asian Symposium on Computer Aided Surgery-Robotic and Image-Guided Surgery, Ibaraki, Japan, 4 pages. (2005).
Zeus, "Robotic Surgical System" available at http://al-laboutroboticsurgery.com/zeusrobot.html.
Charles, et al., Dexterity-enhanced Telerobotic Microsurgery, Advanced Robotics, ICAR '97. Proceedings, 8th Int'l Conference (1997).
ISR & Written Opinion dated Feb. 17, 2016 in Int'l PCT Patent Appl Serial No. PCT/IB2015/002095.
Lang, et al., Intra-operative robotics: NeuroArm., Acta Neurochir Suppl, 109:231-236 (2011).
Mitsuishi, et al., Master-slave robotic platform and its feasibility study for micro-neurosurgery, Int. J. Med. Robot., 9(2):180-9 (2013).
Morita, et al., Microsurgical robotic system for the deep surgical field: development of a prototype and feasibility studies in animal and cadaveric models, J. Neurosurg., 103(2):320-7 (2005).
International Search Report & Written Opinion dated Jul. 10, 2018 in Int'l PCT Patent Appl. Serial No. PCT/IB2018/053272.

* cited by examiner

SURGICAL SYSTEM FOR MICROSURGICAL TECHNIQUES

CROSS-REFERENCE TO RELATED APPLICATIONS

This application is a national phase of International PCT Patent Application No. PCT/IB2015/002095, filed Aug. 27, 2015, which claims priority to U.S. Provisional Patent Application No. 62/042,789, filed on Aug. 27 2014, the entire contents of each of which are incorporated herein by reference.

FIELD OF THE INVENTION

The present invention relates to the field of surgical equipment used to facilitate precise and dexterous manipulation tasks in different surgical procedures, particularly procedures involving microsurgical techniques. Several embodiments relate to mechanical telemanipulators for accomplishing these tasks.

BACKGROUND OF THE INVENTION

Microsurgical techniques are currently employed in several open and minimally invasive surgical procedures. Typical procedures are focused on the restoration of form and function of different parts of the body, and include amelioration of birth defects, hand surgery, maxillofacial surgery, and reconstruction of defects after tumor removal, as well as applications in ophthalmology, neurosurgery, density, cardiovascular surgery and thoracic surgery. Amongst other precise tasks, these microsurgical techniques may consist in reconnecting small and delicate vessels (blood and lymphatic) and nerves (micro anastomosis) such that their function is fully restored. The precision and quality of their execution has an enormous impact on the overall success of the surgery in which they are applied.

A special set of techniques has to be learned by surgeons in order to be able to perform microsurgery, which may be considerably different from the ones used in other conventional "macro" surgical procedures, requiring a continuously high degree of concentration, small movements, and a strained body posture.

With current equipment, the surgical micro techniques are done with the surgeon seated close to the edge of the operating table, with the forearms normally resting on the patient or on the table's top surface. The wrists are placed close to the operation site, the forearms orientated perpendicularly to each other, and the upper arms down and close to the body.

A surgical microscope is positioned above the patient such that its field of view is centered on the surgical area. The image is acquired by the microscope's objective and displayed with magnification to the surgeon through the microscope's eyepieces, which are adjusted in a way that the surgeon can have a balanced sitting position, maintained for long periods of time. Any excessive movement of the head away from the optical axis will result in loss of sight. As an alternative to the surgical microscope, the surgeon might use amplifying loupes, while looking directly at the surgical area.

The instruments for microsurgical techniques are basically aimed at providing a small enough tool to accurately grab and manipulate relevant tissue, needles and suture wires. All instruments are essentially held and actuated like tweezers, being preloaded to an open position, such that a grip is required for the jaws to remain closed. Their control is most effectively achieved when the surgeon is in a comfortable position, resulting in a minimal amount of muscle activity. The forearms should be optimally rested at about a 45-degree-angle in front of the body and the hands should remain steady, while only the fingers are moved. To dampen the physiological tremor at the instrument tip, the instrument should be held as close to the tip as possible and the ring and little finger should be supported on the surface below. However, quite often the surgical area is restricted and an optimal arm and hand posture is not possible, requiring additional skills from the surgeon and imposing additional discomfort to maintain the precision and dexterity of the movements at the instrument's tip.

With existing equipment, microsurgical techniques are considerably demanding and can be physically discomforting to the surgeon over the short and long term, making it an unpopular specialization. While the visualization systems have been improving over time, enabling higher magnifications with increased resolutions, the instruments used for micro surgical techniques haven't followed along the same path of innovation. As a consequence, the precision and dexterity that can be achieved with today's instruments is very much dependent on the surgeon's fine motor skills, which means that from the overall population of qualified surgeons, only a smaller number are able to perform the most delicate operations. Even highly qualified surgeons are not able to have long, active careers due to the degradation of motor skills with age. These issues have been creating a significant mismatch between surgeon capabilities and patient demand, increasing the waiting lists for surgical procedures requiring microsurgical techniques, and limiting the overall adoption of microsurgical techniques despite the fact that better outcomes are often achieved through microsurgery.

To overcome the above-mentioned issue, several surgical robotic systems have been developed with the goal of providing an easier-to-use approach to micro surgical techniques. By means of computerized robotic interfaces, these systems enable the surgeon to improve the control of the instruments, while maintaining surgeon inputs to the surgical decision-making process.

These surgical robotic systems are essentially composed of a combination of master and slave manipulators wherein the master manipulator has position sensors that register the surgeon's hand movements and converts them into electrical signals, which are then processed from the kinematics of the master to the kinematics of the slave and eventually sent to the slave actuators that deliver the motion to the slave manipulator located in the surgical area. By processing and modifying the electrical signals correctly, a robotic master slave system can provide to the surgeon a remote replication of hand movements, with motion scaling and tremor filtering. In addition, they can further provide the surgeon with improved accessibility and a more ergonomic posture during surgery. The master manipulator can also be controlled with an optimal handgrip while the hand is well-supported.

However, although several surgical robotic systems have been developed over the past decades, currently none of them is considered as a viable replacement for conventional equipment in the microsurgical context.

The robotic system disclosed in WO9743942, WO9825666 and US2010011900 is currently the only FDA approved telemanipulator for robotic surgery. While being originally designed for laparoscopic surgery several tests in open microsurgery procedures have been reported in the literature. According to the literature, the robotic master-slave setup is found to be useful in providing scaled down replication of the surgeon's hand movements with reduced tremor, and facilitating the procedure in terms of ergonomics. However, it does not provide force feedback, which, together with the limited access to the patient, raises safety concerns. Another drawback of this system comes from the fact that it is very large, competing for precious space within the operating room environment and significantly increasing preparation time. This limitation, among others, limits workflow integration in the sense that there is no space between adoption of a robotic system, with all of its drawbacks, and having no robotic system in the operating room.

The fact that this system is not compatible with current vision systems for microsurgical techniques, like surgical microscopes and loupes, represents a significant break with current operating room workflow, making impossible the performance of current microsurgical techniques and robotic techniques in the same surgical procedure. This issue is exacerbated by the size and weight of the robotic system.

Several authors have described more compact robotic alternatives (H. Das et al. 1997, M. Lang et al. 2011, A. Morita et al. 2005, M. Mitsuishi et al. 2012, WO2013007784A1), some of them even providing force feedback to the surgeon. However, they typically comprise complex mechatronic or electromechanical systems, with a high number of sensors and actuators, leading to huge costs of acquisition and maintenance, which are actually not affordable for the majority of surgical departments worldwide.

WO 2008130235 discloses a mechanical manipulator for laparoscopy. A parallelogram construction is provided between the proximal end and the distal end of the mechanical master slave systems, creating an unambiguous positional relationship between the handles and the instruments.

The parallelogram constraint imposed by this mechanical manipulator renders it very difficult to obtain a scaled ratio other than 1:1 between the amplitude of the movements applied to the handle of this manipulator and the amplitude of the movements reproduced by the instrument. This limitation reduces drastically its potential use for microsurgical techniques where scaled down ratios are desired for increased precision and tremor reduction.

The mechanical teleoperated device disclosed in WO 2013014621 is able to provide a scaled down replication of the surgeon's movements, with high dexterity and force feedback. However, that disclosed telemanipulator is mainly intended for laparoscopic surgery and, although it can also be applied in open surgery, it is not intended to work in combination with a surgical microscope, magnifying loupes, or even the naked eye.

Several other mechanical systems have been developed for remote manipulation in radioactive environments and are disclosed in several documents, such as U.S. Pat. No. 2,846,084. However, although the system disclosed in this document comprises master-slave architecture, its dimensions, weight and kinematics are not suitable for surgical applications.

Accordingly, an aim of the present invention is to provide a surgical system composed of a mechanical telemanipulator being suitable to work together with visualization systems for microsurgical techniques while overcoming the aforementioned drawbacks of the prior art.

SUMMARY OF THE INVENTION

This aim and other advantages are achieved by a surgical system composed of at least one mechanical telemanipulator for remote manipulation, designed to naturally replicate the surgeon's hand movements in the surgical area, working together with a visualization system for microsurgical techniques, like a surgical microscope or magnifying loupes.

The size and configuration of the mechanical telemanipulator makes it compatible not only with current surgical microscopes but also may ensure a free line of sight between the eyes of the surgeon and the surgical area, enabling the surgeon to visualize the procedure with magnifying loupes or even with the naked eye.

This surgical system may also comprise a solution where a microscope's objective is replaced by an endoscopic camera (in open surgeries) or by a system with digital cameras to acquire an image of the surgical area. The image can then be displayed to the surgeon on a screen (2D or 3D) or through a head-mounted display (or a similar system where a different stereoscopic image is projected on each eye of the surgeon). One of skill in the art will understand that other visualization and imaging systems are possible and that the above are offered as representative examples of apparatuses that could work with the inventive system.

Due to the compatibility with current visualization systems for microsurgery, together with the light weight and the compact configuration of the mechanical telemanipulator, this surgical system can be very easily brought to and removed from the surgical area, enabling its intermittent use on several surgical procedures requiring microsurgical techniques. Therefore, it does not require drastic changes in the workflow and setup of current operating rooms and can be more easily adopted by several surgical teams.

Like a robotic telemanipulator for surgery, the mechanical telemanipulator of this system does not have autonomy or artificial intelligence, being essentially a surgical tool completely controlled by the surgeon. However, this telemanipulator relies on a fully mechanical technology for motion transmission as opposed to robotic systems where commands are transmitted between the master and slave by a computer-controlled mechatronic or electromechanical system. Without electronics, actuators and software, this mechanical telemanipulator is more reliable, affordable to produce and easier to use, benefiting also from more stable force-feedback to the surgeon.

Mechanical transmission allows perfect kinematic matching between the corresponding joints of the slave and master units of the telemanipulator. This master-slave relationship allows the movement of any of the joints of the master unit to be transmitted to the analogous joint of a slave unit. The low inertia of the links of the master and slave units and the low-friction of the mechanical transmission provide backlash-free and ripple-free movements, which gives to the surgeon a realistic rendering of the forces at the distal end of the instruments.

Due to its kinematic model and multi-articulated end-effectors, each telemanipulator allows controlling the surgical instruments with seven degrees of freedom, providing high dexterity to the surgeon. One of skill in the art will understand that other embodiments are possible, such as a telemanipulator system with nine degrees of freedom.

The mechanical telemanipulator is also able to scale down the movements of the surgeon. As a consequence, the physiologic tremors of the surgeon are reduced and the overall precision of the manipulation is increased.

In certain embodiments, the telemanipulators can also have a remote-center-of-motion, enabling the slave unit to be controlled by the master unit, while respecting the constraints imposed by a body incision (minimally invasive surgical procedures), reducing trauma to the patient and improving cosmetic outcomes.

BRIEF DESCRIPTION OF FIGURES

The invention will be better understood thanks to the following detailed description of several embodiments of the invention with reference to the attached drawings, in which.

DETAILED DESCRIPTION OF THE INVENTION

Figure 3:
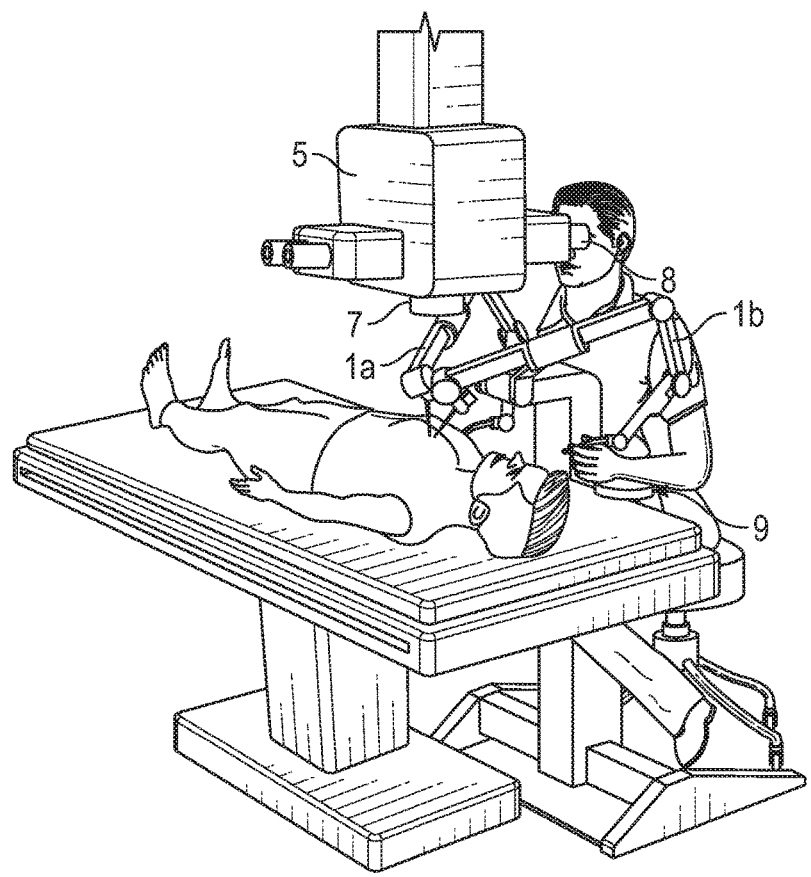
FIG. 3 shows a perspective view of the full surgical system for microsurgical techniques operated by a surgeon during a surgical procedure requiring microsurgical techniques.
Figure 4:
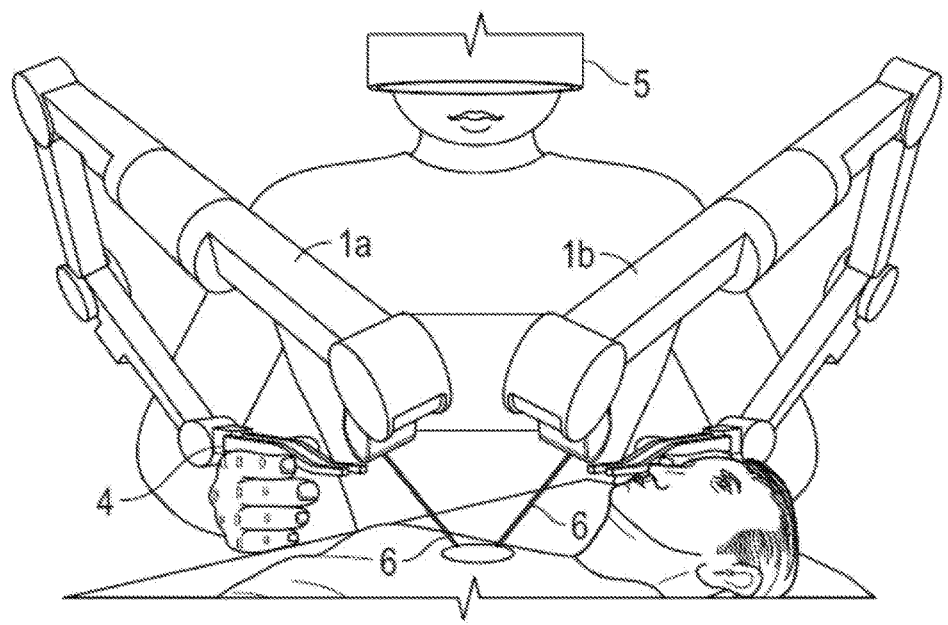
FIG. 4 shows a second perspective view of the full surgical system for microsurgical techniques operated by a surgeon during a surgical procedure requiring microsurgical techniques.

A surgical system for microsurgical techniques, constructed in accordance with a preferred embodiment of the present invention, is described herein, and is seen generally in FIGS. 3 and 4. This system includes preferably two identical mechanical telemanipulators 1a, 1b configured to be operated independently from the other, and a surgical microscope 5 through which the surgeon can have a magnified view of the surgical area, being able to perform microsurgical techniques. While the present embodiment of the inventive system is shown with a surgical microscope, the skilled person will understand that other magnification optics are possible, such as surgical loupes. In certain applications, use of the naked eye for visualization will also be possible.

Figure 1:
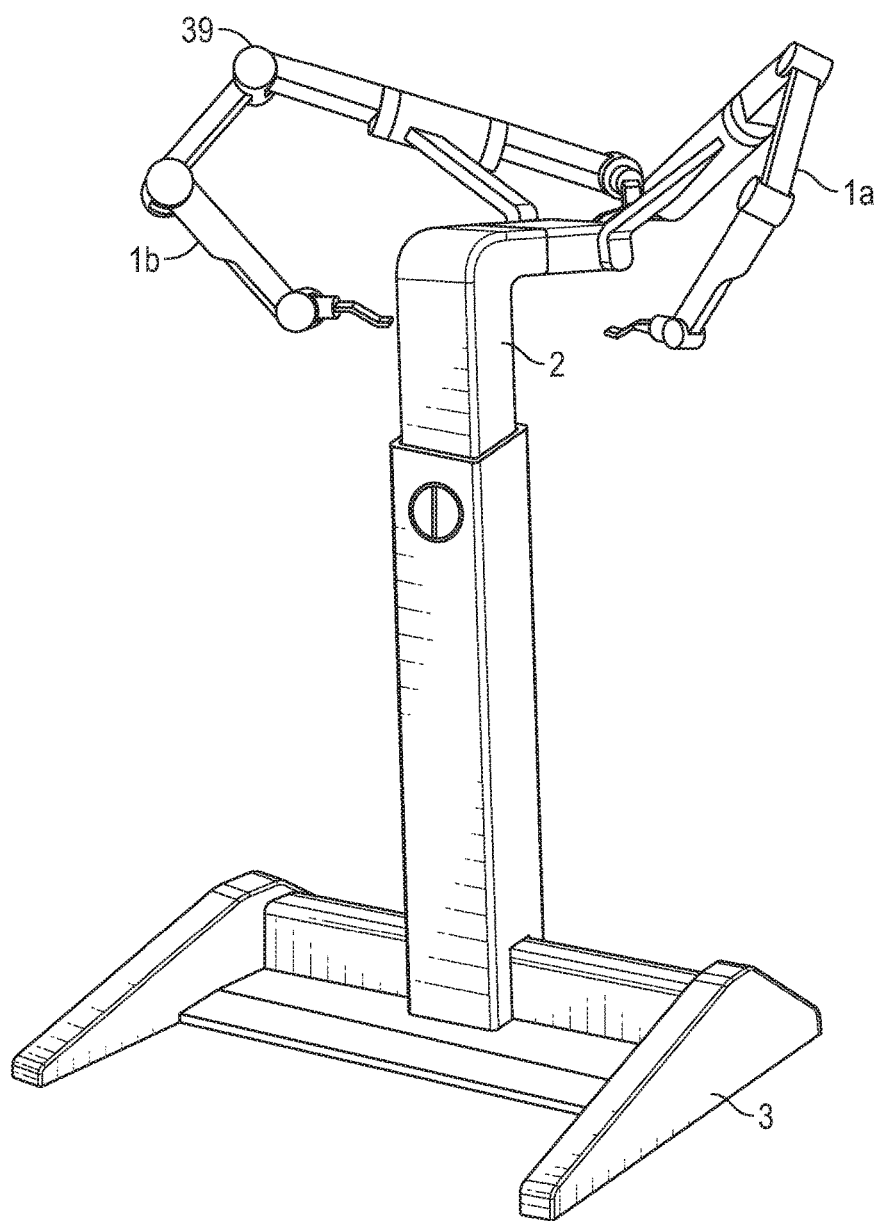
FIG. 1 shows a perspective view of the mechanical telemanipulator composing the surgical system for microsurgical techniques according to a preferred embodiment of the invention.
Figure 2:
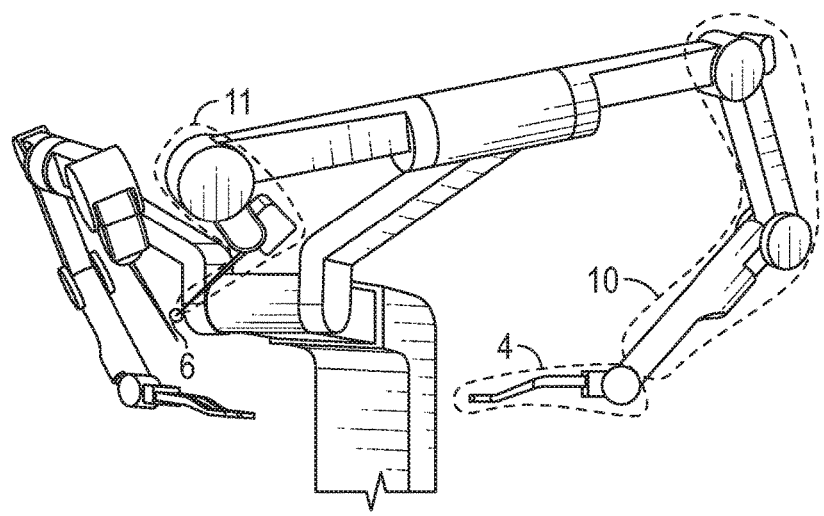
FIG. 2 shows a second perspective view of the mechanical telemanipulator composing the surgical system for microsurgical techniques according to a preferred embodiment of the invention.

According to FIGS. 1 and 2, the two mechanical telemanipulators 1a, 1b are respectively mounted on an articulated structure 2 so that the angles between them and the patient can be tuned and they can be accurately positioned. The articulated structure 2 is mounted on a wheeled base 3, enabling the telemanipulators 1a, 1b to be easily transported and stored within the operating room and hospital. The wheeled base 3 also enables the telemanipulators 1a, 1b to be brought to, and removed from, the surgical area during the part of the surgical procedures requiring microsurgical techniques and precise manipulation. When brought to the surgical area, the articulated structure 2 can be attached to the surgical table with appropriate hardware so that the telemanipulators 1a, 1b can be more steadily supported.

With reference to FIGS. 3 and 4, the surgeon will perform the procedure directly manipulating two handles 4 in the proximal part of each telemanipulator 1a, 1b, viewing the operation through a surgical microscope 5. The movements applied by the surgeon on the two handles 4 (FIG. 6) are replicated (and scaled down) by two multi-articulated surgical instruments 6 (FIG. 7) that reach the surgical area on the patient. Their movements are acquired by the microscope's objective 7 and displayed on the eyepieces 8 as shown in FIG. 3. This surgical system improves the ergonomics for surgeons, enabling them to position their hands in a natural orientation to each other, providing improved hand-eye coordination and intuitive manipulation with scaled down, tremor-reduced movements. The comfort of the surgeons can also be improved by forearm support 9 as shown in FIG. 3.

Figure 11:
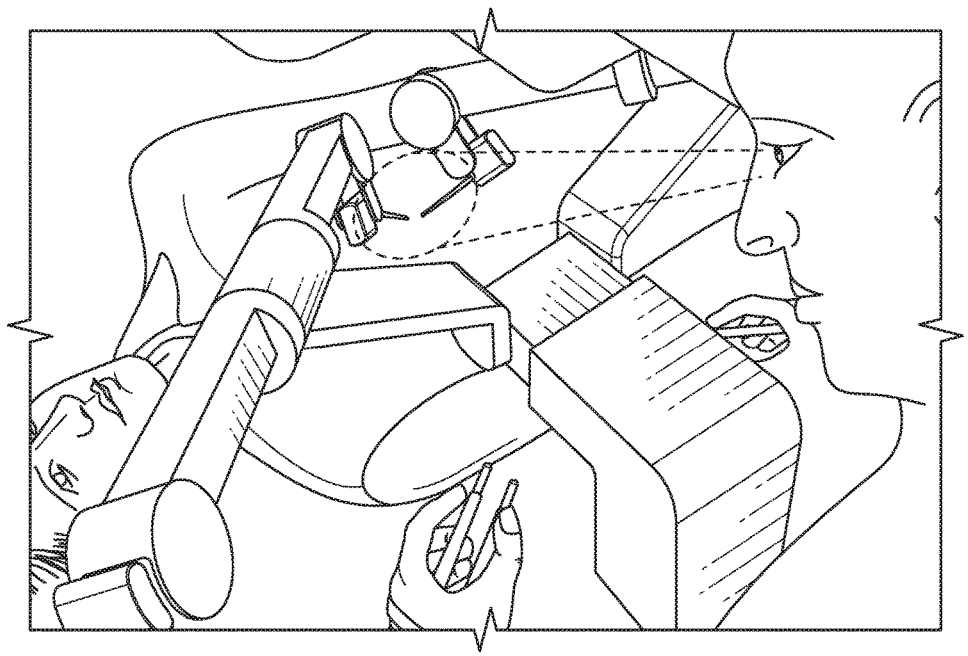
FIG. 11 shows a perspective view of the surgical system for microsurgical techniques where the configuration of the mechanical telemanipulators ensures a free path line between the eyes of the surgeon and the surgical area.

Although the size and configuration of the mechanical telemanipulators 1a, 1b make it compatible with current surgical microscopes 5, they also may ensure a free line of sight between the eyes of the surgeon and the surgical area (FIG. 11), enabling the surgeon to visualize the procedure with magnifying loupes or even with unaided vision.

In another embodiment of this invention, the surgical system may also comprise a solution where the microscope's objective 7 is replaced by an endoscopic camera (in open surgeries) or by a system with digital cameras to acquire the image on the surgical area. The image can then be displayed to the surgeon on a screen (2D or 3D) or through a head-mounted display (or a similar system where a different stereoscopic image is projected on each eye of the surgeon).

The inventive embodiments include a master-slave configuration of each mechanical telemanipulator 1a, 1b. A slave unit 11 and a master unit 10 are configured to work together, achieving a force-reflecting tele-operation. Given that the two telemanipulators 1a, 1b are structurally and functionally identical, the description hereafter will refer to one mechanical telemanipulator only.

Figure 5:
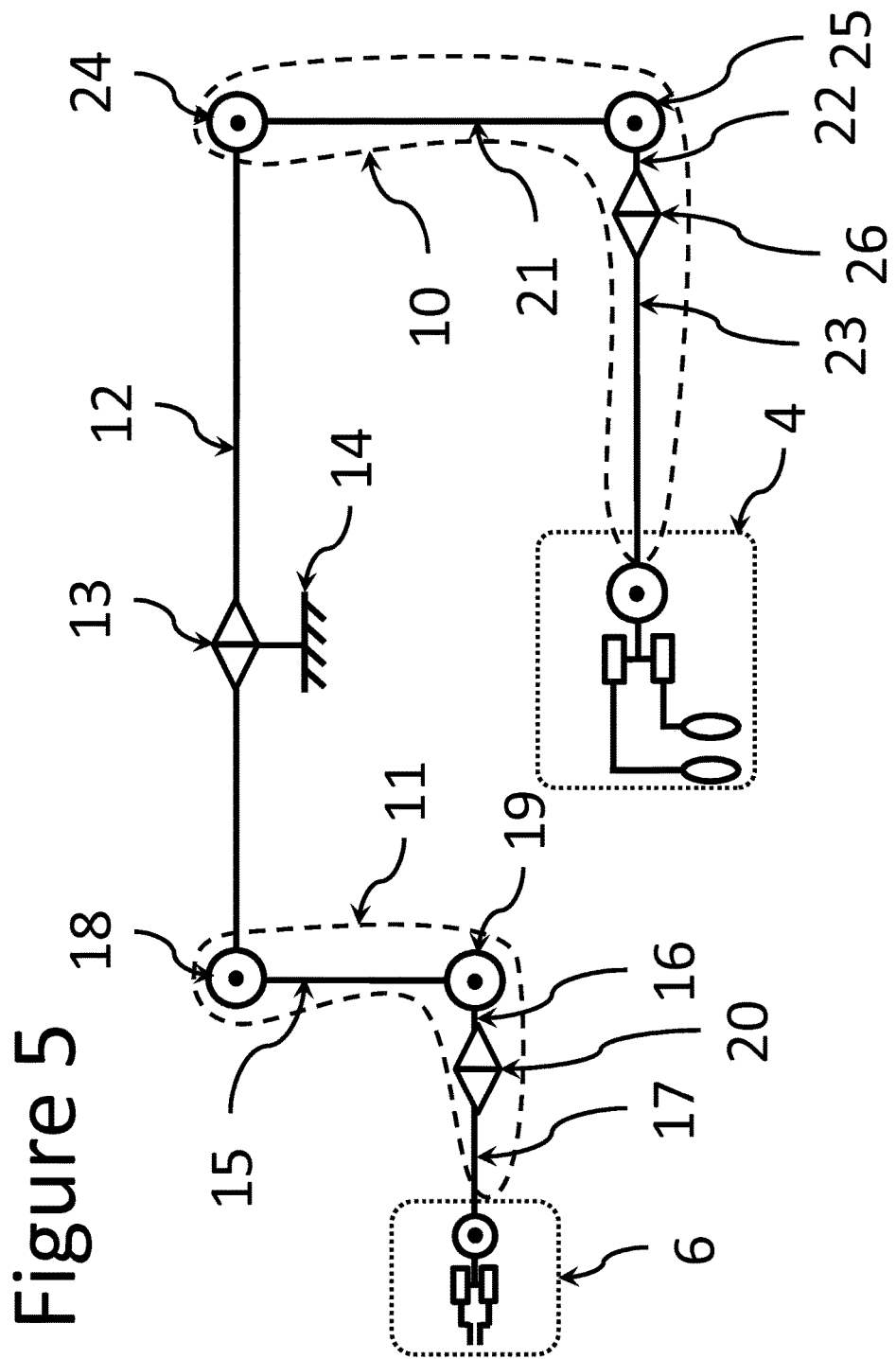
FIG. 5 shows a schematic view with kinematical connections between the corresponding joints of the master and slave units of the mechanical telemanipulator.

FIG. 5 schematically illustrates the kinematic configuration of the teleoperated device according to the preferred embodiment of the invention. This device comprises a slave unit 11 and a master unit 10 connected to each other by a connecting link 12. This connecting link 12 comprises a joint 13 which connects the teleoperated device to a ground 14.

The slave unit 11 comprises a number of slave links 15, 16, 17 interconnected by a plurality of slave joints 18, 19, 20 whereas the master unit 10 comprises a corresponding number of master links 21, 22, 23 interconnected by a plurality of master joints 24, 25, 26. First mechanical transmission means 27, 28, 29 are arranged to kinematically connect the slave unit 11 with the master unit 10 such that the movement (angle of the joint) applied on each master joint 24, 25, 26 of the master unit 10 is reproduced by the corresponding slave joint 18, 19, 20 of the slave unit 11.

In reference to FIG. 5, the multi-articulated end-effector 6 is connected at the distal end of the slave unit 11 whereas the handle 4 is connected at the distal end of the master unit 10 for operating the mechanical teleoperated device wherein the amplitude of the movements applied on the handle 4 by the surgeon is reproduced, at a predetermined scaled ratio, by end-effector 6. Ratios between the slave and the master units 11, 10 can be advantageously chosen according to the use. For instance, not only 1:1 can be used but also 2:1, 4:1 etc. in order to increase the precision of the telemanipulation and filter tremors of the surgeon.

Figure 12:
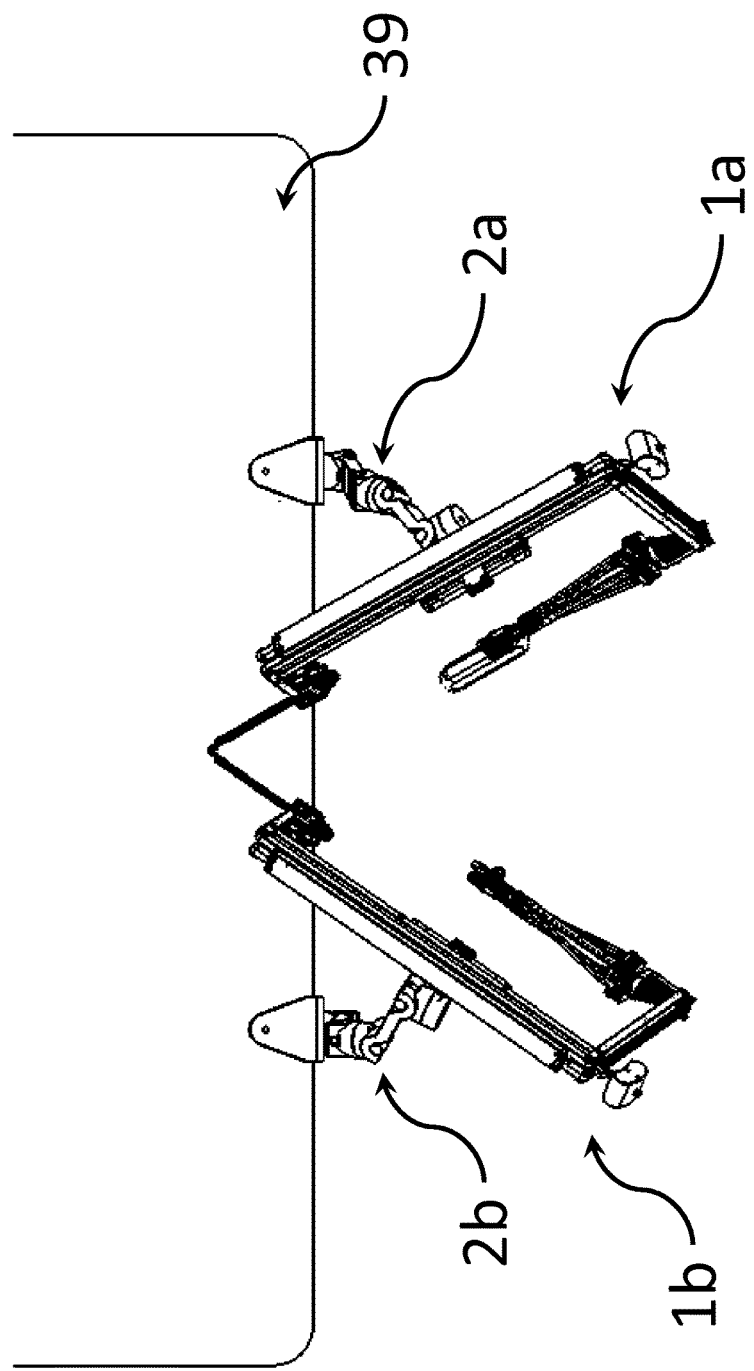
FIGS. 12 to 14 show three different perspective views of the mechanical systems comprising the mechanical telemanipulators.
Figure 13:
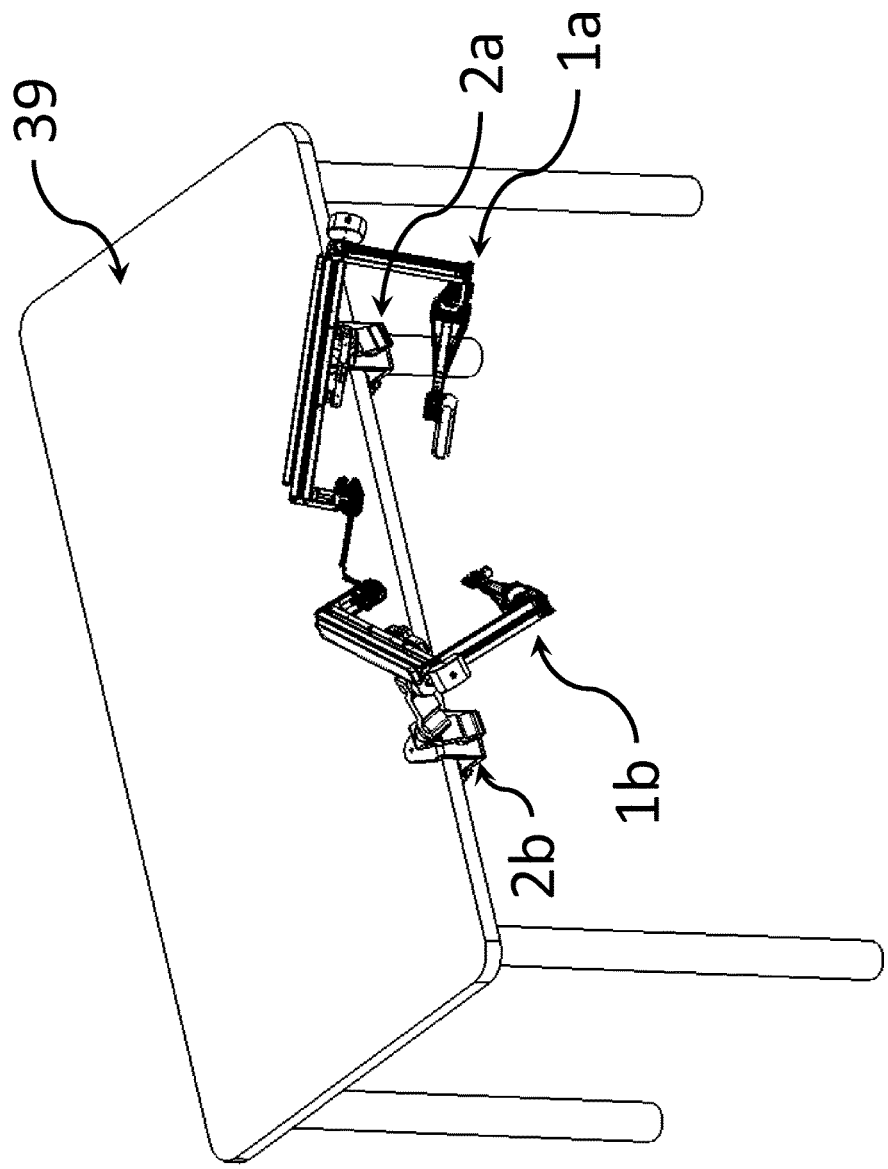
Figure 14:
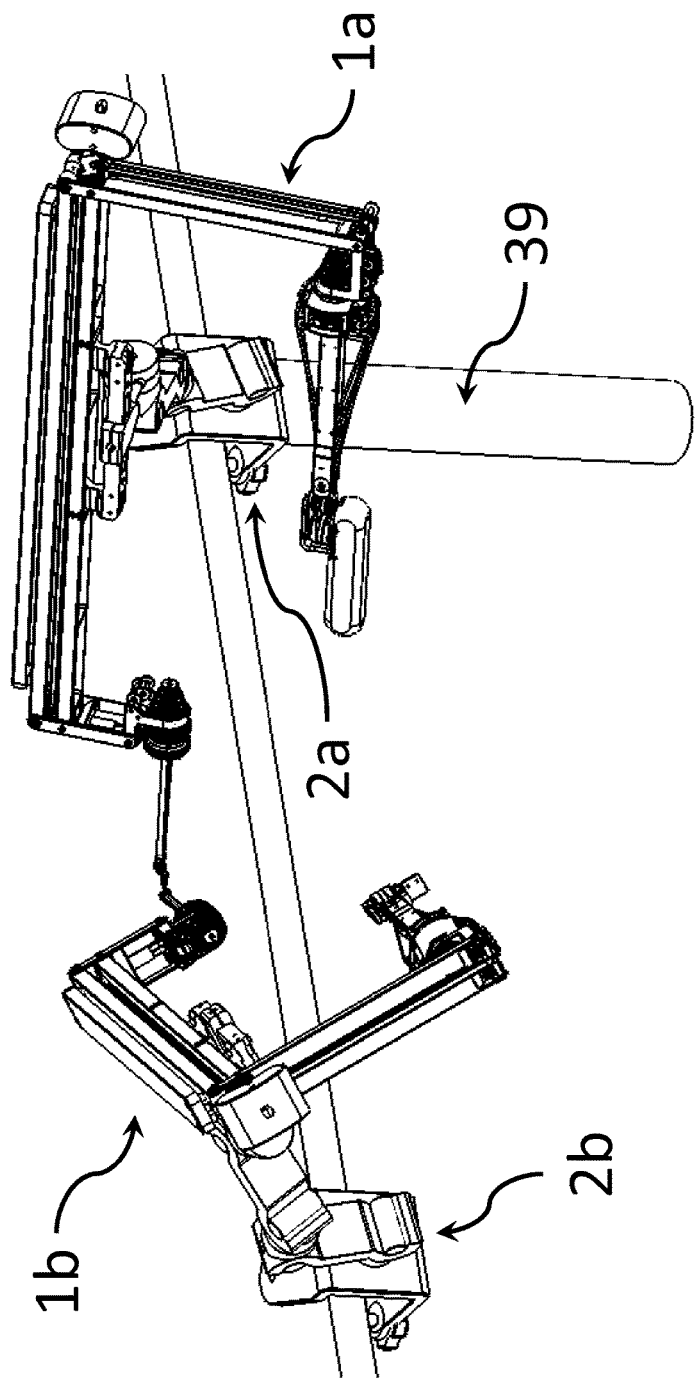

FIGS. 12 to 14 show three different perspective views of the mechanical systems comprising the mechanical telemanipulators 1a, 1b connected to a fixed table by two articulated structures 2a, 2b.

Figure 6:
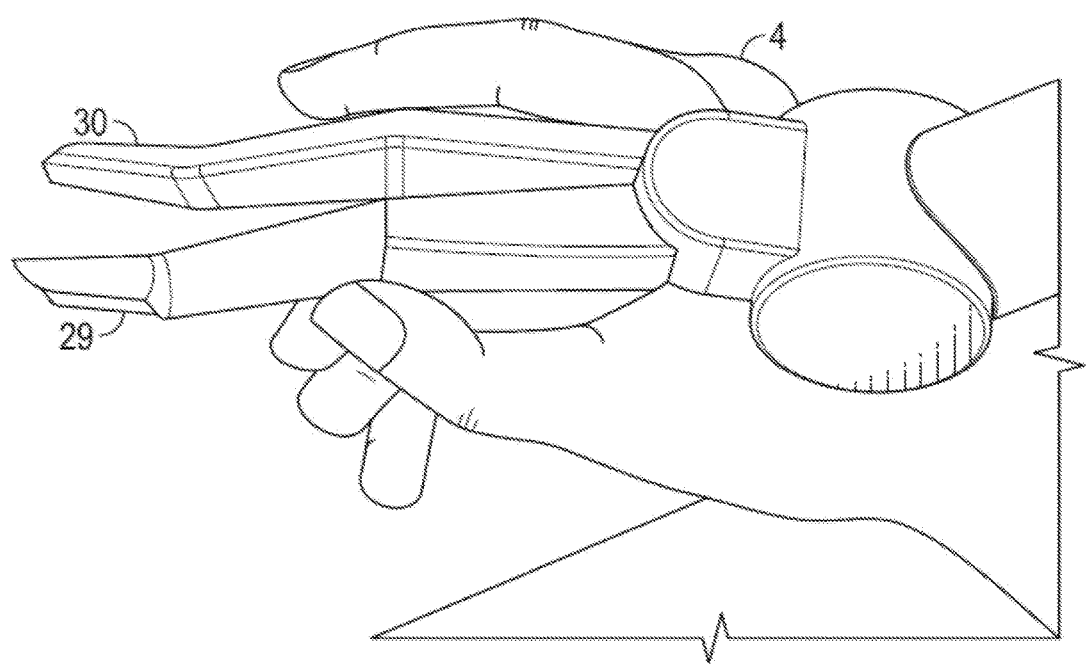
FIG. 6 shows a perspective view of the handle connected to the distal end of the master unit of the mechanical telemanipulator.

With reference to FIG. 6, the handle 4 of the telemanipulator has a configuration similar to a current instrument for microsurgical techniques, with a "tweezers-like" shape.

Figure 7:
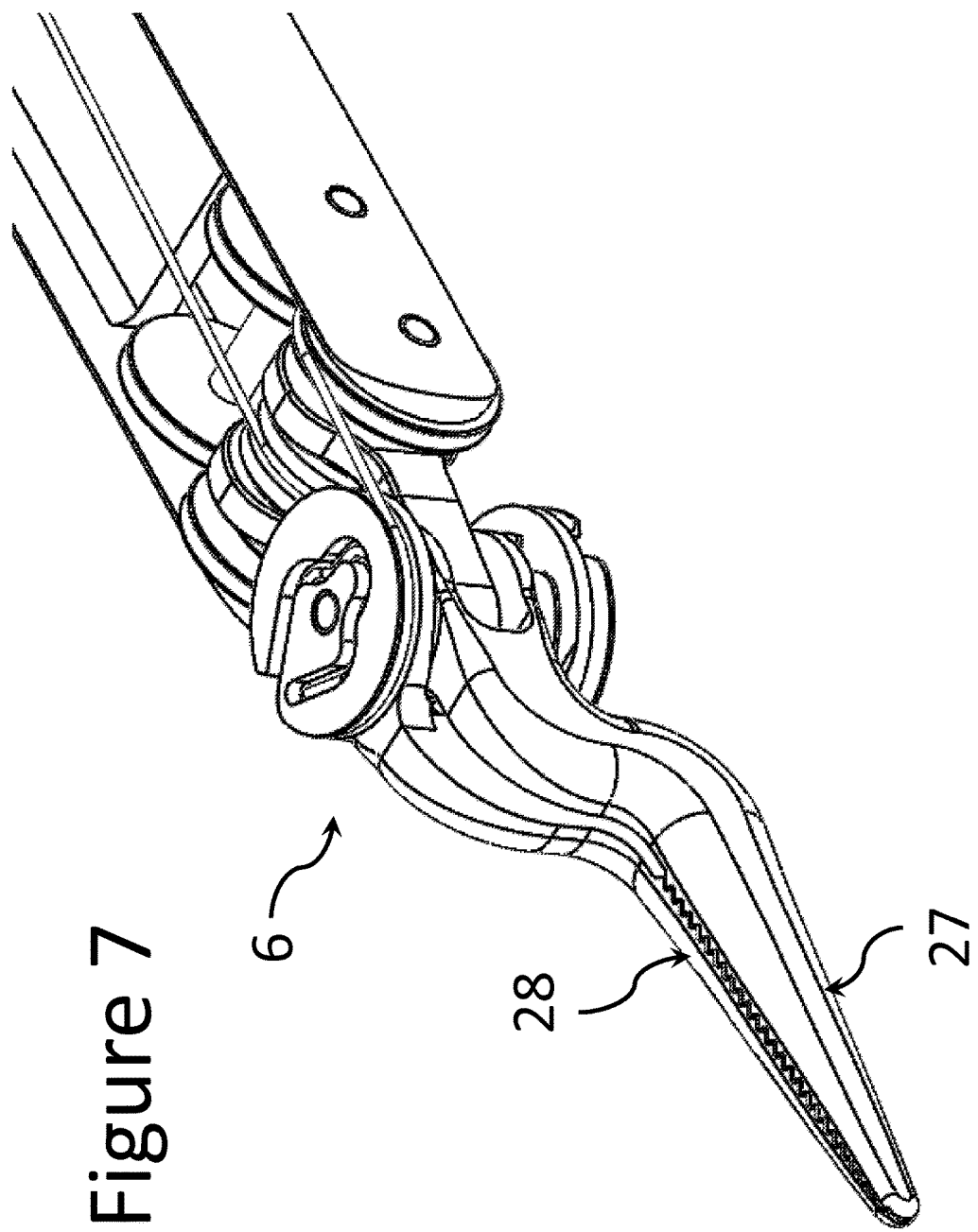
FIG. 7 shows a perspective view of the end-effector connected to the distal end of the slave unit of the mechanical telemanipulator.

The end-effector 6 as shown in FIG. 7 is a surgical tool and comprises two blades 27, 28 coaxially mounted to each other. The handle 4 is kinematically connected to the surgical tool 6 through second mechanical transmission means 31, 32 in a manner that the movement applied on the second and third handle link 29, 30 by the tips of the thumb and the index finger are reproduced by the two blades 27, 28.

The surgical tool 6 is interchangeable and can be of several types, such as scissors, scalpels, cutters, needle holders and other accessories to be connected to the distal end of salve unit 11, like energy surgical instruments suction devices, etc. The surgical tool 6 which enters the patient's body should be bio-compatible and reusable after sterilization. Disposal surgical tool can also be used.

Figure 8:
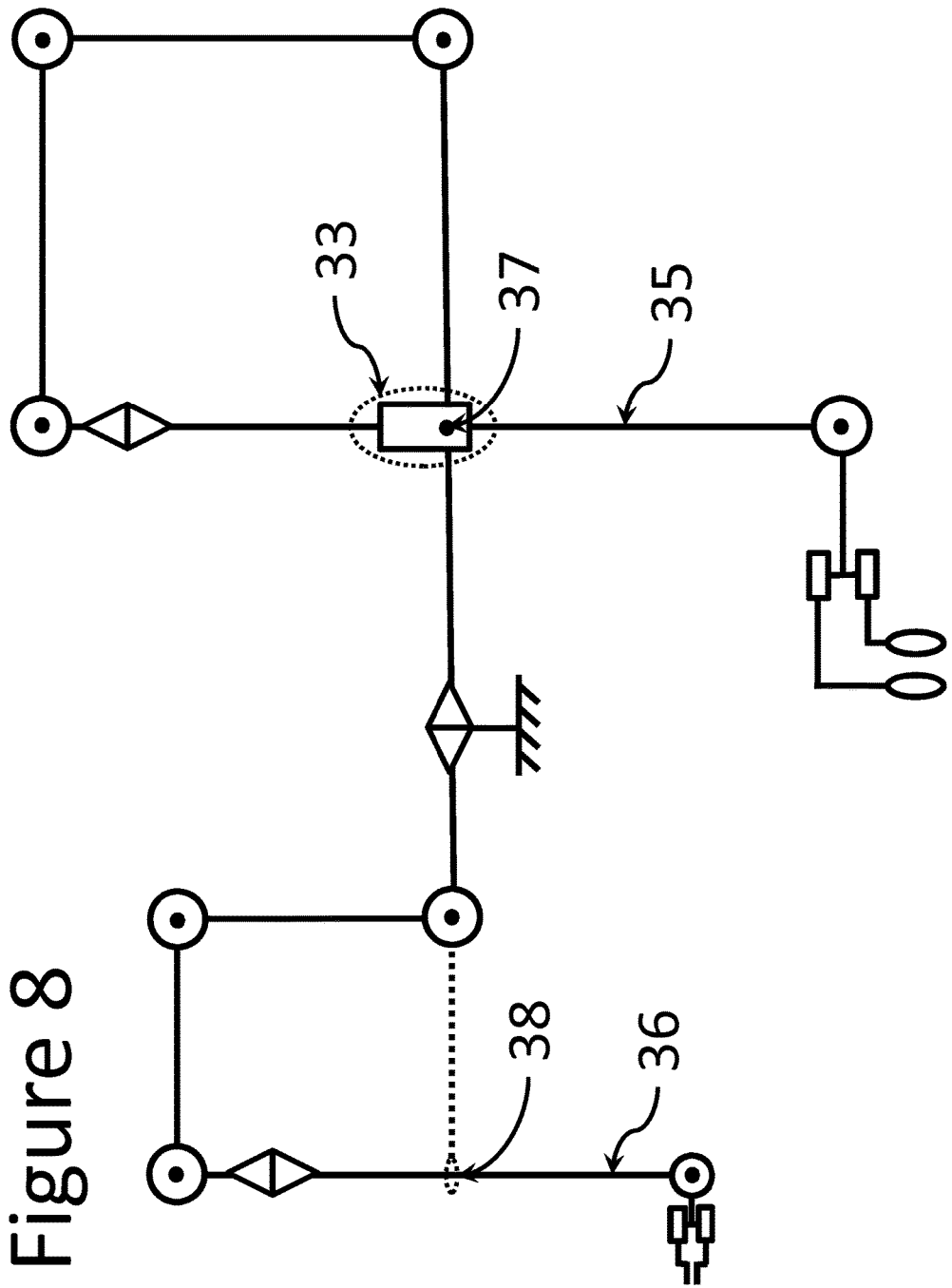
FIG. 8 shows a different possible kinematic configuration of the mechanical telemanipulator according to different embodiments of the invention, having a remote center of motion for minimally invasive surgical procedures.
Figure 9:
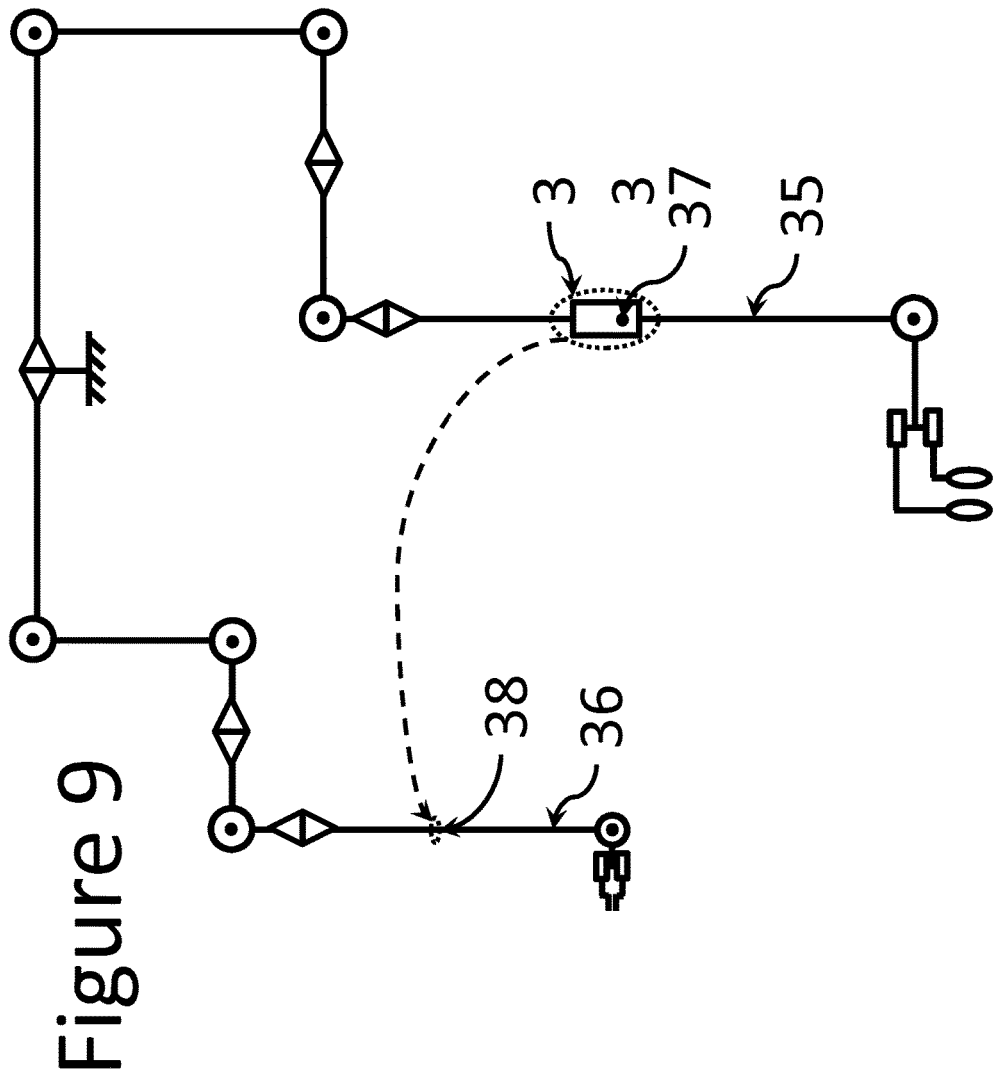
FIG. 9 shows a second different possible kinematic configuration of the mechanical telemanipulator according to different embodiments of the invention, having a remote center of motion for minimally invasive surgical procedures.
Figure 10:
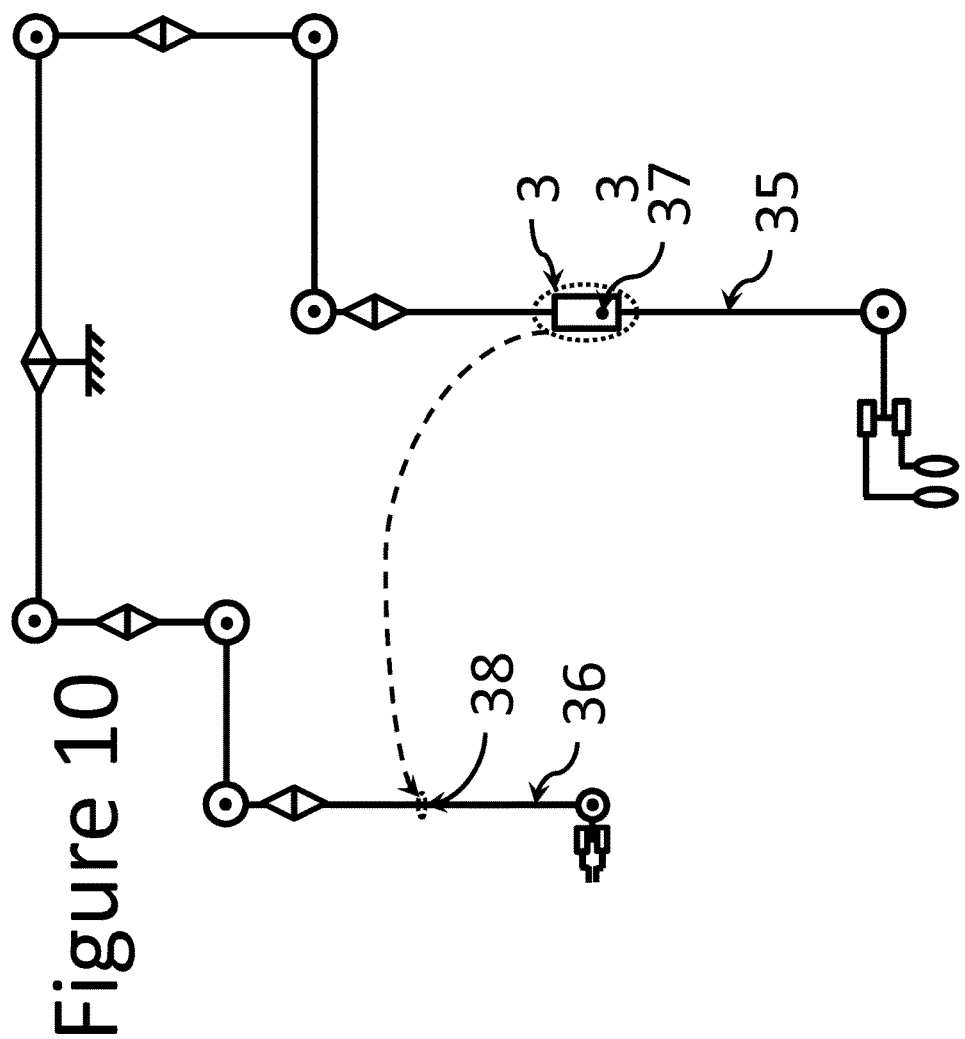
FIG. 10 shows a third different possible kinematic configuration of the mechanical telemanipulator according to different embodiments of the invention, having a remote center of motion for minimally invasive surgical procedures.

In other embodiments of this invention (FIG. 8, FIG. 9 and FIG. 10), there can be constraint means 33 of the teleoperated device which are configured to constrain movements of the distal end of the slave unit so that, when the mechanical telemanipulator is in operation, a certain master link 34 of the master unit 10 always translates along and rotates about a single point 37 so that the corresponding link 36 of the slave unit 11 always translates along and rotates about a single virtual point 38, also known as remote renter of motion, RCM. Even during an open surgical procedure, an RCM 38 or other kinematic constraints can be useful to minimize the clashing of instruments when passing through a narrow body incision (for instance in brain surgery or ENT surgical procedures).

The seven independent degrees of freedom of the telemanipulator according to this preferred embodiment, as thoroughly described hereafter, provide the desired dexterity needed to perform complicated surgical procedures, such as pulling, cutting and/or suturing tissues. With the aim of being as intuitive as possible, the distal degrees of freedom of both the master and slave units 10, 11 are designed to resemble a simplified human forearm, with an articulated wrist and a distal tool.

For each degree of freedom of the mechanical telemanipulator according to the preferred embodiment of the invention, different types of mechanical transmission can be used resulting in the same functional outcome.

Mechanical transmissions means can be partly in the form of pulley-routed flexible elements configured such that each driven pulley of each degree of freedom of the slave unit 11 is connected to the equivalent driving pulley of the master 10 unit, by a single closed cable/tendon loop transmission. A solution using rigid transmission may also be employed, where the transmission is mainly based on articulated linkages or geared elements, which may guarantee an increased stiffness of the system.

The kinematic model of the master and slave manipulators may also take different configurations (for example, the ones shown in FIG. 8, FIG. 9 and FIG. 10) and different number of degrees of freedom, keeping the same principle of working.

In some embodiments, as shown in FIG. 2, counterweights 39 are connected to some links of the master 10 and slave 11 units, in order to compensate the telemanipulator, minimizing gravity forces felt by the surgeon when manipulating the system.

In some embodiments, the mechanical telemanipulator comprises brake means, allowing the system to be fixed in several positions of its workspace, when the surgeon is not holding the handle.

In some embodiments, the mechanical teleoperated device comprises force sensors capable of measuring the forces exerted on the moving links and/or position sensors capable of measuring the movement of the different joints, in order to allow a reconstruction of the movement of the entire telemanipulator.

The surgical system according to the invention has been described for performing microsurgical techniques in different fields of surgery, which can further include ophthalmology, brain surgery, cardiology, orthopedics and dentistry, to name a few.

The surgical system according to the invention could also be employed for any suitable remote actuated application requiring a dexterous manipulation with high precision and dexterity, such as micro-assembly manipulation, manipulation in narrow places, manipulation in dangerous or difficult environments, and manipulation in contaminated or clean environments. In this configuration, the surgical tool may be replaced by a suitable multi-articulated holder or gripper.

Moreover, while this invention has been particularly shown and described with references to particular embodiments thereof, it will be understood by those skilled in the art that various changes in form and details may be made therein without departing from the spirit and scope of the invention as defined by the appended claims.

The invention claimed is:

1. A surgical system for use by a surgeon to perform microsurgical techniques in a surgical area, the system comprising:
   a first telemanipulator having a first proximal end and a first distal end, a first master unit having a first handle coupled to the first proximal end, and a first slave unit having a first end-effector coupled to the first distal end, the first master unit comprising first master links coupled to first slave links of the first slave unit, whereby movement of the first master unit via the first handle by the surgeon is reproduced by the first slave unit to move the first end-effector;
   a second telemanipulator having a second proximal end and a second distal end, a second master unit having a second handle coupled to the second proximal end, and a second slave unit having a second end-effector coupled to the second distal end, the second master unit comprising second master links coupled to second slave links of the second slave unit, whereby movement of the second master unit via the second handle by the surgeon is reproduced by the second slave unit to move the second end-effector; and a visualization system configured to provide the surgeon a free line of sight between the first and second telemanipulators to the surgical area.

2. The surgical system of claim 1, wherein the visualization system includes an image acquisition unit and an image display.

3. The surgical system of claim 2, wherein the image acquisition unit comprises a microscope.

4. The surgical system of claim 2, wherein the image acquisition unit comprises an endoscopic camera.

5. The surgical system of claim 2, wherein the image acquisition unit comprises a system with at least one digital camera.

6. The surgical system of claim 1, further comprising a support structure that supports the first and second telemanipulators.

7. The surgical system of claim 2, wherein the image display comprises a video display screen.

8. The surgical system of claim 2, wherein the image display comprises components that provide a different stereoscopic image to each eye of the surgeon.

9. The surgical system of claim 2, wherein the visualization system comprises a magnifying loupe that allows the surgeon to visualize the surgical area through the free line of sight between the eyes of the surgeon and the surgical area.

10. The surgical system of claim 6, wherein the support structure enables the first and second telemanipulators to be precisely and stably positioned over a patient.

11. The surgical system of claim 10, wherein the support structure is mounted on a wheeled base, enabling the system to be easily brought to and removed from the surgical area during a surgical procedure.

12. The surgical system of claim 1, wherein the amplitude of the movement of the first and second handles by the surgeon is reproduced by the first and second end-effectors at the surgical area at a predetermined scaled down ratio.

13. The surgical system of claim 1, wherein the first telemanipulator comprises a first cable-driven articulated transmission system extending between the first handle and the first end-effector, whereby movement of the first handle by the surgeon is reproduced by the first end-effector at the surgical area, and wherein the second telemanipulator comprises a second cable-driven articulated transmission system extending between the second handle and the second end-effector, whereby movement of the second handle by the surgeon is reproduced by the second end-effector at the surgical area.

14. The surgical system of claim 1, wherein the first and second master links of the first and second master units of the first and second telemanipulators each are connected by respective first and second master joints, wherein the first and second slave links of the first and second slave units of the first and second telemanipulators each are connected by respective first and second slave joints, wherein a number of links and joints in each of the first and second slave units corresponds to a number of links and joints in each of the first and second master units, and wherein motion applied at a particular link or joint in the first or second master unit is reproduced at a corresponding link or joint in the respective first or second slave unit.

15. The surgical system of claim 1, wherein the first and second telemanipulators each further comprises one or more constraints applied to each of the first and second slave units, thus creating a remote center of motion whereby rotation about a predetermined point in the first or second master unit produces rotation about a predetermined point in the respective first or second slave unit.

16. The surgical system of claim 13, wherein the movement of the first handle by the surgeon comprises a movement in at least one of seven degrees of freedom, and wherein the movement of the second handle by the surgeon comprises a movement in at least one of seven degrees of freedom.

* * * * *